United States Patent

Thiele et al.

[11] 4,010,191
[45] Mar. 1, 1977

[54] ACYL DERIVATIVES OF SUBSTITUTED BIS-ARYLALKYLAMINO COMPOUNDS

[75] Inventors: Kurt Thiele, Barcelona, Spain; Walter Von Bebenburg, Frankfurt; Klaus Posselt, Bergen-Enkheim, both of Germany

[73] Assignee: Deutsche Gold-und Silber-Scheideanstalt vormals Roessler, Frankfurt (Main), Germany

[22] Filed: Dec. 14, 1973

[21] Appl. No.: 424,835

Related U.S. Application Data

[63] Continuation of Ser. No. 128,623, Dec. 17, 1970, abandoned.

[30] Foreign Application Priority Data

Dec. 18, 1969 Austria .............................. 787/69

[52] U.S. Cl. ................... 260/471 C; 260/463; 260/469; 260/473 R; 260/479 R; 260/479 S; 260/488 CD; 260/558 P; 260/559 R; 260/562 P; 424/300; 424/301; 424/308; 424/311; 424/312; 424/314; 424/324
[51] Int. Cl.² .............. C07C 103/44; C07C 103/64; C07C 103/82; C07C 125/00
[58] Field of Search ....... 260/471 C, 559 R, 558 R, 260/562 P, 479 R

[56] References Cited

UNITED STATES PATENTS

| 3,167,556 | 1/1965 | Krapcho ................... 260/562 R X |
| 3,337,546 | 8/1967 | Malatestinic et al. ...... 260/562 R X |
| 3,395,143 | 7/1968 | Thiele et al. ............... 260/562 R X |
| 3,574,211 | 4/1971 | Keck et al. ................. 260/562 A X |
| 3,574,749 | 4/1971 | Howe et al. ................ 260/562 P |
| 3,646,145 | 2/1972 | Thiele ......................... 260/570.5 C |

FOREIGN PATENTS OR APPLICATIONS

630,296 10/1963 Belgium ..................... 260/570.5 C

OTHER PUBLICATIONS

Thiele et al., Arzneimittel Forschung, vol. 18, pp. 1255-1263.

*Primary Examiner*—Richard L. Raymond
*Attorney, Agent, or Firm*—Michael J. Striker

[57] ABSTRACT

Compounds of the formula

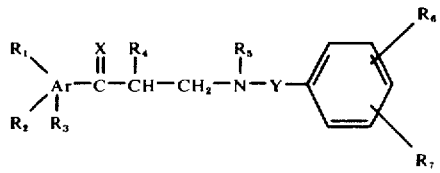

wherein Ar is phenyl or naphthyl, X is oxygen or the group

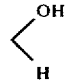

Y is substituted or unsubstituted alkylene of 1–4 carbon atoms, $R_1$ is acyloxy, acyloxyalkoxy, acylamino or is —N(Alkyl)(Acyl), $R_4$ is hydrogen or lower alkyl, $R_5$ is hydrogen, lower alkyl or acyl, and $R_2$, $R_3$, $R_6$ and $R_7$ are the same or different and are hydrogen, halogen, hydroxy, lower alkoxy, acyloxy, amino, alkylamino, dialkylamino, acylamino, nitro, lower alkyl, lower halogeno alkyl, or lower alkylthio,
acyl in these radicals being derived from [a] saturated or unsaturated, straight, or branched, substituted or unsubstituted fatty acids of 2–10 carbon atms, [b] substituted or unsubstituted benzoic acids, [c] lower aliphatic mono esters of carbonic acid, or [d] the carbonic acid phenyl mono ester; and pharmaceutically acceptable salts of these compounds; optically active isomers thereof and diastereomers.

The compounds have antiphlogistic, analgesic, antipyretic, broncholytic and coronary circulation regulatory action.

7 Claims, No Drawings

ACYL DERIVATIVES OF SUBSTITUTED BIS-ARYLALKYLAMINO COMPOUNDS

REFERENCE TO RELATED APPLICATION

This application is a continuation of application Ser. No. 128,623, filed Dec. 17, 1970, which is now abandoned.

SUMMARY OF THE INVENTION

The invention resides in novel compounds of the formula

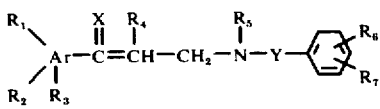  (I)

wherein Ar is phenyl or naphthyl, X is oxygen or the group

Y is substituted or unsubstituted alkylene of 1–4 carbon atoms, $R_1$ is acyloxy, acyloxyalkoxy, acylamino or is —N(Alkyl)(Acyl), $R_4$ is hydrogen or lower alkyl, $R_5$ is hydrogen, lower alkyl or acyl, and $R_2$, $R_3$, $R_6$ and $R_7$ are the same or different and are hydrogen, halogen, hydroxy, lower alkoxy, acyloxy, amino, alkylamino, dialkylamino, acylamino, nitro, lower alkyl, lower halogeno alkyl, or lower alkylthio, acyl in these radicals being derived from [a] saturated or unsaturated, straight or branched, substituted or unsubstituted fatty acids of 2–10 carbon atoms, [b] substituted or unsubstituted benzoic acids, [c] lower aliphatic mono esters of carbonic acid, or [d] the carbonic acid phenyl mono ester;

and pharmaceutically acceptable salts of these compounds; optically active isomers thereof and diastereomers.

The invention also embraces various processes for making the above compounds. The compounds may for instance be made by reacting [a] compounds of the formula

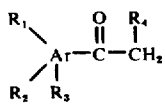  (II)

with [b] a compound of the formula

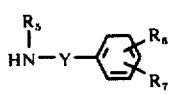  (III)

wherein Ar, Y and $R_1$ to $R_7$ have the same meaning as above with [c] formaldehyde or a precursor of formaldehyde.

The invention furthermore comprises pharmaceutical compositions including the above compounds as the active agent and a method for treating patients requiring antiphlogistic treatment or requiring treatment with a broncholytic or coronary regulatory agent by administering the compounds as defined above.

DETAILED DESCRIPTION OF THE INVENTION AND OF PREFERRED EMBODIMENTS

If $R_2$, $R_3$, $R_7$ in the above compounds are lower halogeno alkyl, they may for instance be trifluoromethyl.

Regarding the various acyl groups that may be present in the compounds, the following is noted: If acyl is derived from fatty acids, these may be substituted, for instance, by halogen, hydroxy, acylated hydroxy, oxo, lower alkoxy or phenyl. Phenyl itself, in this case, may also be substituted by alkyl of 1–6 carbon atoms, alkoxy of 1–6 carbon atoms, hydroxy or halogen.

If benzoic acids, that is benzene-derived acids, form the acyl group, these acids may be substituted in at least one place by halogen, hydroxy, acylated hydroxy, lower alkyl or lower alkoxy.

In the radical identified as Y, this group may be substituted likewise by halogen, hydroxy, lower alkoxy or acyloxy. In general Y can be straight or branched and saturated or unsaturated. Y in particular may be one of the groups as follows:

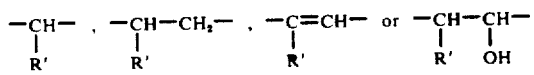

wherein R' is hydrogen, methyl or ethyl.

If acyl is derived from a fatty acid as defined above, which is substituted by a phenylic group, such as for instance cinnamic acid, α-methylcinnamic acid or α-ethylcinnamic acid, the phenyl group present in these radicals in turn may itself be substituted by alkyl of 1–6 carbon atoms, preferably methyl, alkoxy of 1–6 carbon atoms, preferably methoxy, hydroxy or halogen, particularly chlorine or fluorine. In general, and unless otherwise specifically noted, alkylene in the compounds of the invention may have 1–4 carbon atoms, alkyl may have 1–6 carbon atoms, and if acyl is derived from a fatty acid, the acid may have from 2 to 10 carbon atoms. This applies also where alkyl forms part of another group such as alkoxy or where it is present in, for instance, aliphatic mono esters (half esters) of carbonic acid.

Wherever acylamino is mentioned, it should be understood that the second hydrogen atom attached to nitrogen in this group may likewise be substituted by alkyl

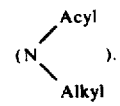

The compounds of the invention may be made in various ways.

A. A compound of the formula

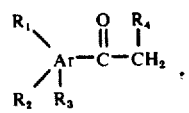  (II)

may be reacted with a compound of the formula

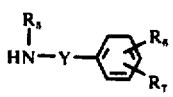

wherein Ar, Y and $R_1$ to $R_7$ have the meaning as above, and formaldehyde or a precursor of formaldehyde.

B. A compound of the formula

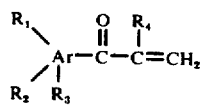

or the corresponding Mannich base of the formula

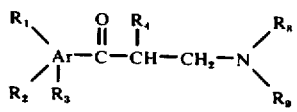

wherein Ar and $R_1$ to $R_4$ have the meaning as above, and $R_8$ and $R_9$ are lower alkyl or together form a cycloalkyl group, may be reached with a compound of the above-given formula (III).

C. A compound of the formula

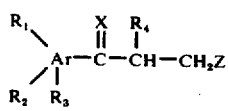

may be reacted with a compound of the formula

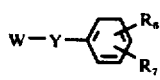

wherein Ar, X, Y and $R_1$ to $R_7$ have the meaning as above and Z and W are different and are either halogen or $-NHR_5$. This reaction is carried out in the presence of a basic medium.

D. A compound of the formula

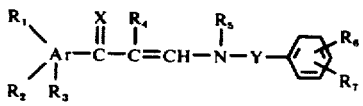

wherein the symbols Ar, X, Y and $R_1$ to $R_7$ have the meaning as above, may be subjected to reduction of the CC-double bond.

E. A compound of the general formula (I) given above wherein Ar, X, Y and $R_2$ to $R_7$ have the meaning as above wherein, however, a nitro group is present instead of $R_1$, may be subjected to reduction of at least this nitro group to an amino group followed by acylation.

F. A compound of the general formula (I) wherein Ar, X, Y and $R_2$ to $R_7$ have again the meaning as above, wherein, however, there is present an oxy-, oxyalkyl, amino-, or monoalkylamino group may be subjected to acylation of these groups present in the stead of $R_1$.

The compounds obtained in all of these processes may then be subjected to reduction of any of all oxo groups that may be present to form hydroxyl groups and/or the thusformed hydroxyl groups or other hydroxyl or amino groups may be subjected to acylation in subsequent process steps.

The compounds can furthermore be converted into pharmaceutically acceptable salts. As anions for the salts, there may be used the usual therapeutically acceptable acid residues.

Regarding the conditions of the reaction, the following is noted:

The process above identified as [A] is usually carried out in a temperature range between 20° and 150° C. As solvents in this process there may be used, for instance, alcohols, dioxane, glacial acetic acid ester, etc.

The process [B] is preferably carried out at a temperature between 0° and 80° C, if an unsaturated ketone is used, and in an inert solvent, for instance ether, acetone, dioxane or chloroform. If, however, the corresponding Mannich base as identified above by formula (V) is used, the reaction temperature should be between 30° and 120° C, and the solvent may for instance be water, an alcohol/water mixture or a twophase system such as water/benzene or water/toluene.

The process identified above as [C] is carried out in a temperature range between 20° and 140° C in a solvent or suspension agent such as alcohols, ethers, dimethylformamide, dimethylsulfoxide, etc. As basic reagents which are used in this case there may be employed: alkali alcoholates, alkali amides, alkali carbonates, tertiary amines, etc.

The reduction of the CC-double bond according to the above process [D] is preferably carried out in a conventional organic solvent by hydrogenation in the presence of platinum-containing catalysts such as platinum, platinum oxide, platinum supported by a carbonaceous carrier. The reaction is effected at a slightly increased temperature, generally within the range between about 30° and 70° C. Preferred are temperatures between 30° and 50° C. The pressure for the hydrogenation may be between normal pressure and 20 atm. above atmospheric pressure. Usually, atmospheric pressure is sufficient. The employed solvent preferably is polar. The hydrogenation is carried out until the necessary theoretical amount of hydrogen is absorbed in order to saturate the double bond.

The reduction in the process [E] can be carried out with hydrogen in the presence of a catalyst such as palladium, platinum oxide, Raney nickel, etc. at temperatures between 20° and 100° C and atmospheric pressure, and in a solvent such as alcohols, an alcohol/water mixture or glacial acetic acid or with nascent hydrogen (zinc/HCl, Fe/HCl).

The acylation of the hydroxy and/or amino groups is carried out in conventional manner by converting this corresponding acid or a functional derivative of such acid, such as a halide, anhydride, amide, ester or ketene. This reaction may be carried out with or without a solvent at temperatures between 0° and 300° C. If free acids are used, the temperatures are preferred to be above 100° C. As solvents there may be used, for instance, alcohols, aromatic hydrocarbons, dioxane, tetrahydrofuran, aliphatic ethers, dimethylsulfoxide, aliphatic ketones, N-methyl pyrrolidone, sulfolane, etc. At times it is advisable in this operation to add basic materials such as alkali hydroxides or earth alkali metal hydroxides or corresponding alcoholates, carbonates or acetates, or tertiary amines or pyrridine, etc. However, basic agents are not necessary if ketenes, esters or the free acids are used.

The hydroxy or amino groups present in the molecule have different reactivity, depending on the position. This therefore permits a selective acylation. The aromatic amino groups are easiest to acylate. Selective acylation of these amino groups can, for instance, be effected by reaction with equimolar amounts of acid chloride or -anhydride in an inert solvent, for instance ether, acetone, dimethylformamide, etc. without or with addition of an equimolar amount of an acid acceptor, for instance pyridine, triethylamine, etc. The reaction is carried out in these cases at low temperatures, for instance between 0° and 20° C.

Aromatic amino and aromatic hydroxyl groups are for instance acylated with the calculated amount of acid chloride in the presence of aqueous alkali hydroxide at a temperature between 0° and 30° C or with an equimolar amount of acid chloride or -anhydride in a solvent, for instance ether, dioxane, dimethylformamide, and in the presence of an excess of an acid acceptor, for instance pyridine, or triethylamine, at a temperature, for instance, between 0° and 30° C.

Under somewhat harsher conditions, it is also possible to acylate hydroxy groups which are non-aromatic. In this case, for instance, an excess of acid chloride or -anhydride is used in a solvent such as dioxane, chloroform and in the presence of an excess of an acid acceptor, for instance pyridine, triethylamine or in the presence of pyridine as solution promotor or without solvent. The reaction is preferably carried out at an increased temperature such as between 40° and 140° C.

The reduction of oxo groups can be effected with hydrogen in the presence of a catalyst such as palladium, platinum oxide, Raney nickel, at temperatures between 20° and 100° C and a pressure between 1 and 50 atm. in a solvent such as alcohol, glacial acetic acid, etc. As chemical reducing agent there may be used hydrides, particularly alkali hydrides and complex alkali hydrides such as sodium boron hydride, lithium aluminum hydride, etc. or alcoholates such as aluminum isopropylate. The solvents may be water, alcohols or ethers. The temperature preferably is between 0° and 150° C.

The thus-obtained compositions, which contain optically active carbon atoms and normally are obtained as racemates, can be separated in conventional manner, for instance by means of an optically active acid, into the optically active isomers.

It is, however, also possible to use right at the beginning optically active or also diastereomeric starting products. The final product in this case will be obtained in the pure optically active form or as a diastereomeric configuration.

MAKING OF THE STARTING PRODUCTS

The starting products for the process identified above as [F] may for instance be made as described in Belgian Pat. Nos. 630,296, 730,433, 733,213 and Spanish Pat. No. 355,604.

The starting products for the above process [D] may for instance be obtained by reacting a compound of the formula

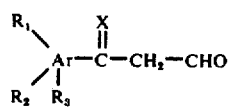

or the corresponding alkali-enolate with a compound of the formula

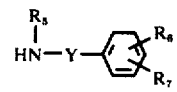

in a solvent such as water or an alcohol. The alkali-enolate may be obtained from the corresponding acetophenone and ethylformate in the presence of sodium.

UTILITY

As already briefly noted, compounds of the invention have an antiphlogistic, analgesic, antipyretic, broncholytic and coronary regulating action.

The antiphogistic action has in particular been observed, in addition to the regulatory action for the coronary circulation, in compounds wherein $R_1$ is an acylamino group. The same applies to compounds wherein $R_1$ is acyl derived from an unsaturated acid and compounds wherein Y is substituted by hydroxyl. A strong antiphlogistic action has also been observed in compounds wherein, for instance, one of the radicals $R_6$ or $R_7$ includes a hydroxy group, particularly if it is in the para-position.

Other compounds are distinguished by their broncholytic and coronary regulatory action, and usually have also an antiphlogistic action, though this may be comparatively weak. Examples of these latter compounds are those wherein $R_1$ is acyloxy. The different properties and pharmacological action of the compounds of the invention were established by the following tests.

1. Antiphlogistic action

The compounds were tested by the familiar Carrageenin-Edema test of the rat paw employing the method of Domenjoz et al. (Arch. exp. Pharm. Path. 230 (1957) 325). The compounds were administered in this test by mouth in a dosage range from 1 to 500 mg/kg. A strong antiphlogistic action was found. The compounds with the highest action resulted in an edema reduction of about 50% at a dose between 3 and 10 mg/kg by mouth.

To compare the antiphlogistic action, the well known antiphlogisticum salicylamide may be used which has a similar action only at a considerably higher dosage when compared with both of the present compounds.

2. Heart and circulatory action

The compounds of the invention were tested in detached guinea pig hearts by the method of Langendorff (Pflüger's Arch. 61 (1895) 291) in respect of the coronary flow, the inotropic action and the heart frequency. Also there were tested in anaesthetized dogs which had been subjected to a thoracostomy.

The significant parameters of the heart and circulatory activity in this case were determined by means of electromagnetic flux measurement and pressure measurement in the interior of the heart ventricle.

With the Langendorff-Hearts the compounds effected a coronary dilation with simultaneous increase of the contractive power in the dosage range between 5 and 500 mg per heart. In the anaesthetized dogs the compounds effected a clear increase of the contractive power of the heart, noticeable by an increase of the heart-time volume and the quotient dp/dt with an oral dosage range between 0.01 to 5 mg/kg in case of i.v. application and a range between 0.5 and 50 mg/kg by oral administration. There is simultaneously a substantial and lasting increased blood flow through the coronary system. The compounds are therefore highly useful to improve the performance as well as the circulation within the heart.

Comparative tests were carried out with papverine which, however, has a smaller inotropy and a substantially shorter duration of action compared with the compounds of the present invention.

3. Broncholytic action

These tests were carried out with detached tracheas obtained from guinea pigs by the method of Castillo and de Beer (J. Pharm. Therap. 90 (1947) 104. The principle of this method consists in the lowering or elimination of the histamine spasm by addition of the particular compound to be tested. The compounds of the present invention in these tests had a bronchospasmolytic action within the dosage range of $2.5 \times 10^{-6}$ to $8 \times 10^{-5}$ g/ml solution.

For comparative tests papaverine was again used which, however, had an action of substantially shorter duration compared to the compounds of the invention.

4. Toxicity

The acute toxicity was determined by the method of Miller and Tainer (Proc. Soc. Exper. Biol. Med. 57 (1944) p. 261. With rats this toxicity, expressed as the $LD_{50}$ in mg/kg in case of oral application is between 100 and 5000 mg/kg. With mice the same test showed an oral toxicity between 100 and 5000 mg/kg and in case of intraperitoneal administration between 10 and 2000 mg/kg.

PHARMACEUTICAL COMPOSITIONS

Pharmaceutical compositions wherein the compounds of the invention are the active ingredient may be formed with the usual pharmaceutically acceptable carrier agents and additives. Compounds of the invention may be used singly or in mixture between different compounds, and they may also be employed in mixture with other pharmacologically or pharmaceutically active materials.

Regarding the type of carrier materials and adjuncts, reference is made to Ullmanns "Encyklopaedie der technischen Chemie," Vol. 4 (1953), pages 1–39; Journal of Pharmaceutical Sciences, Vol. 52 (1963), p. 918, etc.; H. v. Czetsch-Lindewald, "Hilfsstoffe fuer Pharmazie und angrenzende Gebiete," and Pharm. Ind. issue 2, 1961, page 72, etc.

Examples for such carrier materials are gelatines, cane sugar, pectin, mono- or polybasic alcohols, such as glycols, glycerine, diethylgycol, pentaerythrite, sorbitol, mannitol, etc. The latter may also be etherified. Also useful are benzyl benzoate, dioxolanes, glycerineformales, glycolfurfural, dimethylacetamide, lactamides, lactates, ethyl carbonates, etc.

In addition, preservatives, buffer compounds, flavoring agents, anti-oxidants and complexing agents (for instance ethylene diaminotetraacetic acid) and similar materials may be added.

As antioxidants there may for instance be used sodium metabisulfite and ascorbic acid. As preservatives there may be used for instance sorbic acid, p-hydroxybenzoic acid ester, etc.

The composition may be applied enterally, parenterally, orally, perlingually or in form of sprays. According to the use they may be set up in the form of tablets, capsules, pills, lozenges, suppositories, liquid solutions or aerosols. When applied in liquid form the compounds may be set as up as oily or aqueous solutions, as suspensions, emulsions, etc.

Other pharmaceutical compounds may be included in the compositions.

The making of the pharmaceutical compositions follows the conventional standard methods.

By way of a summary survey, the following are the pathological conditions in which the application of the compounds of the invention may be indicated.

As anti-inflammatory agents:

chronic polyarthritis
diseases of the rheumatic syndrome
post-traumatic inflammations
swellings in case of fractures
thrombophlebitis in any form including post-operative occurrence
bursitis
synovitis
collagenosies such as polymyositis, periarteritis
gout As circulatory regulative agents:

coronary insufficiency
angina pectoris
myocardiac infarct

As broncholytic agents:

bronchialasthma
bronchopulmonary diseases with asthmatic component

The pharmaceutical compositions usually contain between 1 and 50% of the active components of the invention;

Preferably the compounds are in the form of tablets containing between 5 and 100 mg or solutions containing between 0.1 and 2.5% of active ingredient.

The unit dose of the active ingredient should for instance be 50 in case of oral application and 5 mg in case of intravenous application, calculated with relation to the free base. This dose can be administered once or several times daily.

For instance, 1–3 tablets can be applied three times daily with a contents of 50 mg of active agent in case of oral application, and 1–3 times daily in the form of an ampule of 2 ml contents containing 5 mg active agent for the purpose of the intravenous administration.

The following examples will further illustrate the invention.

EXAMPLE 1

1-β-[1-Phenyl-1-hydroxy-propyl-(2)-amino]-3-acetoxy-propiophenone

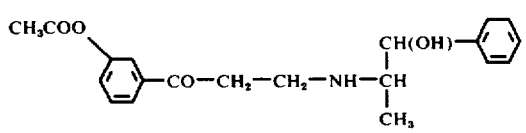

17.8 g (0.1 mol) 3-acetoxy-acetophenone, 3 g paraformaldehyde and 18.7 g (0.1 mol) l-morephedrine.HCl were subjected to boiling in 150 ml isopropanol for 2 hours upon reflux. After thirty minutes, another 2 g paraformaldehyde were added. Upon cooling the HCl salt precipitated and was recrystallized from methanol. m.p. 205°–206° C.

EXAMPLE 2

1-β-[1-Phenyl-1-hydroxy-propyl-(2)-amino]-3-trimethylacetoxy-propiophenone

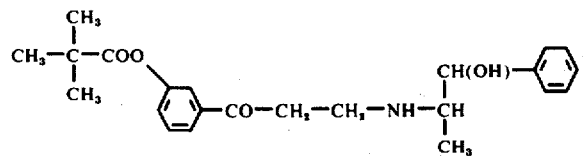

33 g (0.15 mol) 3-trimethylacetoxy-acetophenone, 5 + 2 g paraformaldehyde and 28 g (0.15 mol) 1-norephedrine.HCl were reacted in 100 ml isopropanol in the manner described in Example 1. The HCl salt was recrystallized from ethanol. m.p. 199°–200° C.

EXAMPLE 3

1-β-[1-phenyl-1-hydroxy-propyl-(2)-amino]-3-enanthoyloxy-propiophenone

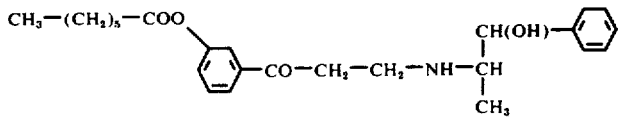

37.6 g (0.15 mol) 3-enanthoyloxy-acetophenone, 5 + 2 g paraformaldehyde and 28 g (0.15 mol) l-norephedrine.HCl were reacted in 100 ml isopropanol as in Example 1. The HCl salt was recrystallized from ethanol. m.p. 168°–170° C.

EXAMPLE 4

1-β-[1-Phenyl-1-hydroxy-propyl-(2)-amino]-3-γ-chlorbutyryloxy)-propiophenone

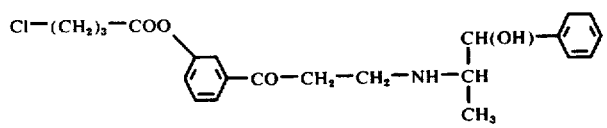

24.5 g (0.1 mol) 3-(γ-chlorobutyryloxy)-acetophenone, 6 g paraformaldehyde and 18.7 g (0.1 mol) l-norephedrin.HCl were heated in 100 ml isopropanol upon addition of two drops of glacial acetic acid ester for a period of 3 hours under reflux conditions. After each hour, additional 6 g paraformaldehyde were added. The solvent was distilled off, the residue successively treated with ether and water, and the residual HCl salt recrystallized from isopropanol/methanol. m.p. 181°–182° C.

EXAMPLE 5 l-β-[1-phenyl-1-hydroxy-propyl-(2)-amino]-4-(-chlorobutyryloxy)-propiophenone

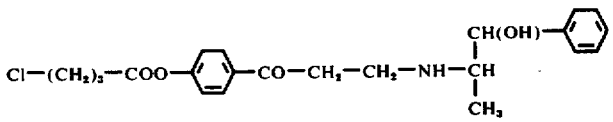

24.5 g (0.1 mol) 4-(γ-chloro-butyryloxy)-acetophenone, 3 × 6 g paraformaldehyde and 18.7 g (0.1 mol) 1-norephedrine.HCl were reacted in 100 ml isopropanol upon addition of two drops glacial acetic acid ester similar to Example 4 and further treated as described there. The HCl salt was recrystallized from isopropanol. m.p. 175°–176° C.

EXAMPLE 6

1-β-[1-Phenyl-1-hydroxy-propyl-(2)-amino]-3-methoxyacetoxy-propiophenone

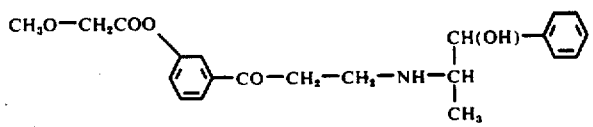

32 g (0.158 mol) 3-methoxyacetoxy-acetophenone, 6 = 3 g paraformaldehyde and 28.8 g (0.158 mol) l-norephedrine.HCl were reacted in 150 ml isopropanol in the manner of Example 1. The HCl salt was recrystallized from ethanol. m.p. 188°-189° C.

EXAMPLE 7

1-β-[1-Phenyl-1-hydroxy-propyl-(2)-amino]-3-diphenylacetoxy-propiophenone

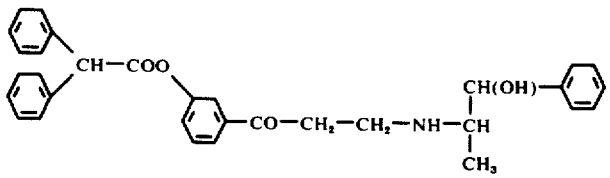

61 g (0.185 mol) 3-diphenylacetoxy-acetophenone, 6 + 3 g paraformaldehyde and 34.6 g (0.185 mol) l-norephedrine.HCl were reacted in 220 ml isopropanol in the manner of Example 1. The HCl salt was recrystallized from methanol. m.p. 190°-191° C.

EXAMPLE 8

1-β-[1-Phenyl-1-hydroxy-propyl-(2)-amino]-2-(4-anisoyloxy)-propiophenone

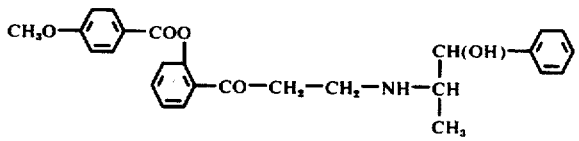

25 g (0.092 mol) 2-(4-anisoyloxy)-acetophenone, 3 + 3 g paraformaldehyde and 15.7 g (0.084 mol) l-norephedrine.HCl were in 60 ml isopropanol in the manner of Example 1. The HCl salt was precipitated with 100 ml acetone and recrystallized from methanol. M.p. 183°-185° C.

EXAMPLE 9

1-β-[1-Phenyl-1-hydroxy-propyl-(2)-amino]-3-(3-anisoyloxy)-propiophenone

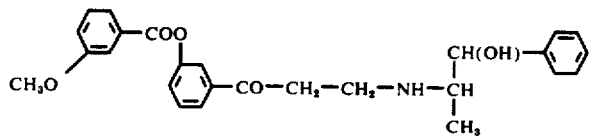

25.8 g (0.1 mol) 3-(3-anisoyloxy)-acetophenone, 3 + 2 g paraformaldehyde and 18.7 g (0.1 mol) l-norephedrine.HCl were reacted in 150 ml isopropanol in the manner of Example 1. The HCl was recrystallized from methanol. m.p. 193°-194° C.

EXAMPLE 10

1-β-[1-Phenyl-1-hydroxy-propyl-(2)-amino]-3,5-diacetoxy-propiophenone

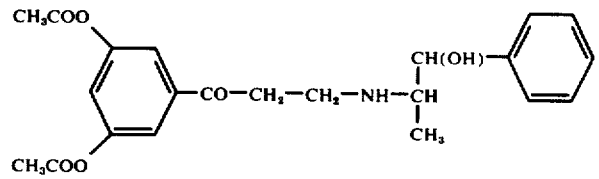

23.6 g (0.1 mol) 3,5-diacetoxy-acetophenone, 3 + 2 g paraformaldehyde and 18.7 g (0.1 mol) l-norephedrine.HCl were reacted in 50 ml isopropanol in the manner described in Example 1. The HCl salt was recrystallized from methanol. m.p. 204°-205° C.

EXAMPLE 11

1-β-[1-Phenyl-1-hydroxy-propyl-(2)-amino]-3-(2-acetocy-ethoxy)-propiophenone

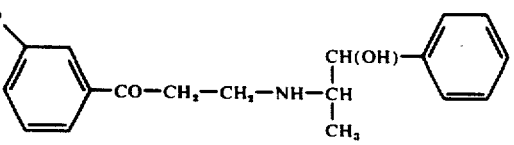

26.9 g (0.11 mol) 3-(2-acetoxy-ethoxy)-acetophenone, 3 + 2 g paraformaldehyde and 18.7 g (0.1 mol) l-norephedrine.HCl were reacted in 60 ml isopropanol in the manner of Example 1. The HCl salt was recrystallized from methanol. m.p. 184°–186° C.

EXAMPLE 12

1-β-[1-phenyl-1-hydroxy-propyl-(2)-amino]-1-acetoxy-propionaphthone-(2)

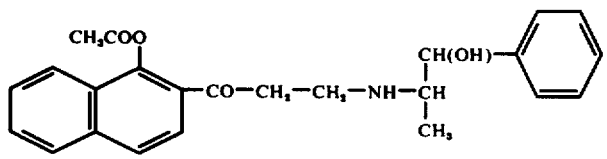

33 g (0.145 mol) 1-acetoxy-acetonaphthone-(2), 4.5 + 4.5 g paraformaldehyde and 27 g (0.45 mol) 1-norephedrine.HCl were reacted in 100 ml isopropanol in the manner of Example 1. The HCl salt was precipitated with acetone and recrystallized from isopropanol. m.p. 177°–178° C.

EXAMPLE 13

1-β-[1-phenyl-1-hydroxy-propyl-(2)-amino]-4-acetoxy-propionaphthone-(1)

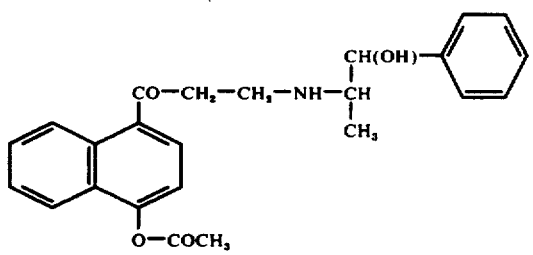

36 g (0.158 mol) 4-acetoxy-acetonaphthone-(1), 4.5 + 4.5 g paraformaldehyde and 29.4 g (0.158 mol) 1-norephedrine.HCl were reacted in 100 ml isopropanol in the manner of Example 1. The HCl salt was precipitated with acetone and recrystallized from ethanol. m.p. 191°–192° C.

EXAMPLE 14

1-β-[1-Phenyl-1-hydroxy-propyl-(2)-amino]-3-acetamino-propiophenone

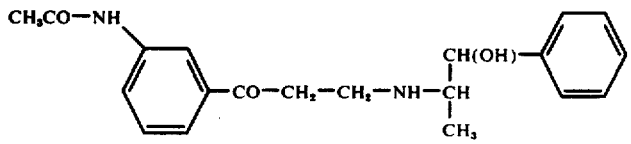

17.7 g (0.1 mol) 3-acetamino-acetophenone, 3 + 1.5 g paraformaldehyde and 18.7 g (0.1 mol) 1-norephedrine.HCl were reacted in 50 ml isopropanol as described in Example 1. The solvent was distilled off and the residual HCl salt was recrystallized from acetone. m.p. 180°–181° C.

EXAMPLE 15 d,l-β-[1-(4-hydroxy-phenyl)-1-hydroxy-propyl-(2)-amino]-3-(β,β-dimethyl-acryloylamino)-propiophenone

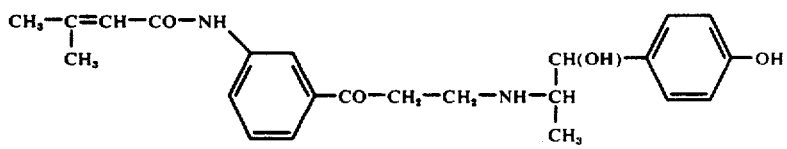

52 g (0.24 mol) 3-(β,β-dimethyl-acryloylamino)-acetophenone, 7.8 g (0.26 mol) paraformaldehyde and 40.6 g (0.2 mol) d,l-4-hydroxy-norephedrine.HCl were heated for 2 hours from reflux in 200 ml isopropanol. Thereafter about 100 ml isopropanol were distilled off and the residue was reacted with 100 ml acetone. The precipitated HCl salt was stirred into 200 ml water, removed by suction, washed with acetone and recrystallized from methanol. m.p. 200° C.

EXAMPLE 16

1-β-[1-Phenyl-1-hydroxy-propyl-(2)-amino]-3-(β,β-dimethylacryloylamino)-propiophenone

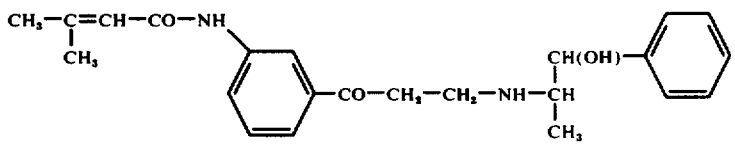

21.7 g (0.1 mol) 3-(β,β-dimethylacryloylamino)-acetophenone, 3.9 g (0.13 mol) paraformaldehyde and 18.7 g (0.1 mol) 1-norephedrine.HCl were heated and refluxed in 100 ml isopropanol for 6 hours. After cooling down the mass was reacted with ether and the precipitated HCl salt was recrystallized from isopropanol. m.p. 164° C.

EXAMPLE 17

1-β-[1-Phenyl-1-hydroxy-propyl-(2)-amino]-4-(β,β-dimethylacryloylamino)-propiophenone

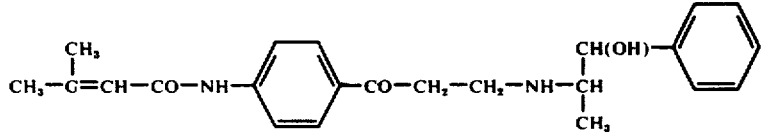

21.7 g (0.1 mol) 4-(β,β-dimethyl-acryloylamino)-acetophenone, 3.9 g (0.13 mol) paraformaldehyde and 18.7 g (0.1 mol) l-norephedrine were heated and refluxed in 120 ml isopropanol for 6 hours. After cooling down, the mass was reacted with water and the precipitated HCl salt was removed by suction and recrystallized from methanol. m.p. 217°–218° C.

EXAMPLE 18 d,l-β-[1-(4-Hydroxy-phenyl)-1-hydroxy-propyl-(2)-amino]-4-(β,β-dimethyl-acryloylamino)-propiophe-

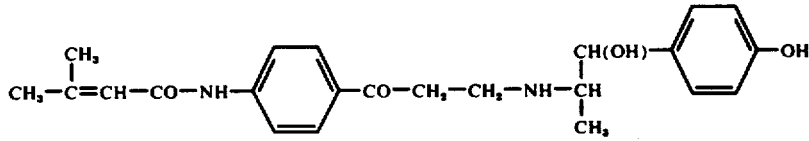

21.7 g (0.1 mol) 4-(β,β-dimethyl-acryloylamino)-acetophenone, 3.9 g (0.13 mol) paraformaldehyde and 20.3 g (0.1 mol) d,l-4-hydroxy-norephedrine.HCl were heated in 150 ml isopropanol for 2 hours while refluxing. Then, about 100 ml isopropanol was distilled off and the residue was reacted with 100 ml acetone. The precipitated HCl salt was mixed by stirring with 200 ml water, then removed by suction, thereafter washed with acetone and recrystallized from methanol. m.p. 210°–211° C.

EXAMPLE 19

1-β-[1-Phenyl-1-hydroxy-propyl-(2)-amino]-2-(β,β-dimethylacryloylamino)-propiophenone

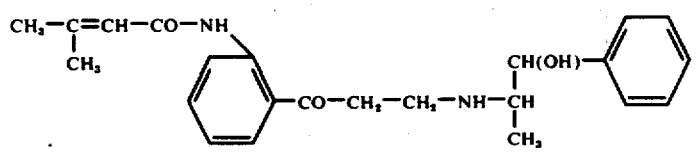

16 g (0.074 mol) 2-(β,β-dimethyl-acryloylamino)-acetophenone, 2.9 g (0.96 mol) paraformaldehyde and 13.8 g (0.074 mol) l-norephedrine.HCl were heated and refluxed for 6 hours in 50 ml isopropanol. After cooling down the mass was reacted with ether and the precipitated HCl salt was recrystallized from methanol. m.p. 218° C.

EXAMPLE 20 d,l-β-[1-(4-Hydroxy-phenyl)-1-hydroxy-propyl-(2)-amino]-4-carbathoxyamino-propiophenone

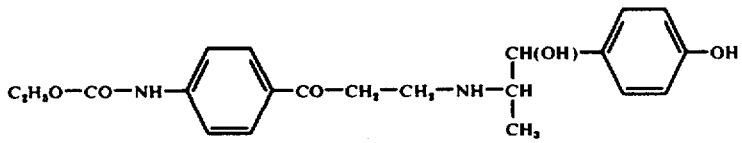

62.1 g (0.3 mol) 4-carbethoxyamino-acetophenone, 11.7 g (0.39 mol) paraformaldehyde and 60.9 g (0.3 mol) d,l-4-hydroxy-norephedrine.HCl were heated and refluxed for 3 hours in 300 ml isopropanol. The HCl salt precipitated upon cooling and was recrystallized from methanol. The yield was 19 g. m.p. 198° C.

EXAMPLE 21

β-(p-Nethoxybenzylamino)-3-(3,3-dimethyla-cryloylamino)-propiophenone

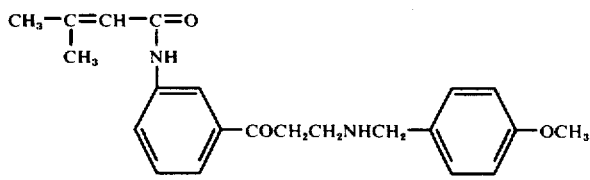

31 g (0.1 mol) β-dimethylamino-3-(3,3-dimethyla-cryloylamino)-propiophenone.HCl were dissolved in 120 ml water and 40 ml ethanol while being heated. 13.7 g of p-methoxybenzylamine were added dissolved in 40 ml ethanol. A ter 2 minutes an oil separated out of the clear solution which had a temperature of about 30° C. While standing overnight the oil crystallized and was removed by suction. The crude product was dissolved in a small amount of ethanol, diluted with the same amount of methanol and cooled. This caused the Mannich base to crystallize out. The purification was repeated twice so as to obtain a pure product. The melting point was 136° C.

EXAMPLE 22

β-(2-phenyl-ethylamino)-3-(3,3-dimethyla-cryloylamino)-propiophenone

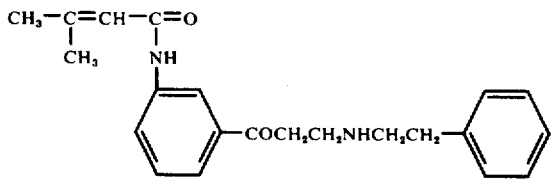

31 g (0.1 mol) β-dimethylamino-3-(3,3-dimethyla-cryloylamino)-propiophenone.HCl + 12.1 g phenethyl-amine were reacted as described in other examples in a water/ethanol mixture. The mass was diluted with water after 5 hours and the oily phase which separated was taken up in ether. The ether solution was washed three times with water. The Mannich base then crystallized from the ether solution and was subjected to precipitation from methanol-ether in the form of the fumarate. The fumarate was recrystallized from isopropanol and ethanol. The melting point was 100° C.

EXAMPLE 23

β-(2-Phenyl-1-methyl-ethylamino)-3-(3,3-dimethyla-cryloylamino-propiophenone

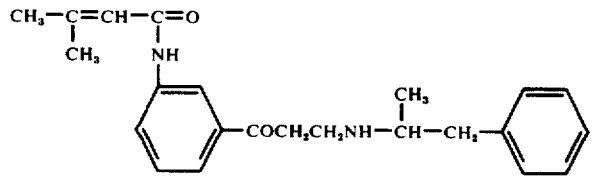

31 g β-dimethylamino-3-(3,3-dimethylacryloylamino)-propiophenone. HCl + 13.5 amphetamine were mixed. After a short time an oil separated out. The oil was taken up in ether, diluted with methanol and the Mannich base was precipitated in the form of the fumarate. The fumarate was recrystallized from methanol-H$_2$O and from methanol-ether. Melting point 110° C.

EXAMPLE 24

1-[2-(4-Chlorophenyl)-2-hydroxyethylamino]-3-(β,β-dimethylacrylylamino)propiophenone

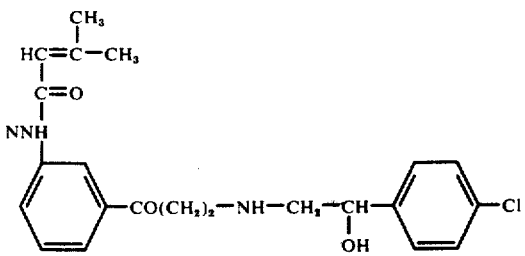

31 g β-dimethylamino-3-(3,3-dimethylacryloylamino-propiophenone. Hydrochloride and 17 g of 2-(4-chlorophenyl)-2-hydroxyethylamine were stirred at 50° C for 30 minutes into a water-methanol mixture (300 ml, ratio 2:1). The syrupy oil which separated was dissolved in ether. The free base crystallized out after a short period of time in pure form. M.P. 139°-140° C.

EXAMPLE 25

β-[2-(4-methylphenyl)-2-hydroxyethylamino]-3-(β,β-dimethylacrylylamino)propiophenone

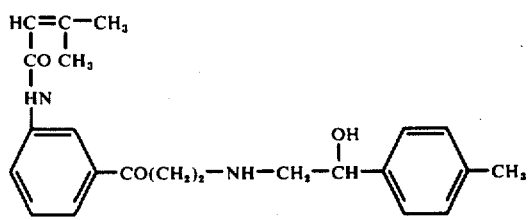

31 g β-dimethylamino-3-(3,3-dimethylacryloylamino)-propiophenone hydrochloride and 15 g of 2-(4-methylphenyl)-2-hydroxyethylamine were stirred at 50° C for 30 minutes into a water-methanol mixture (300 ml. ratio 2:1). The oil that separated out was decanted and dissolved in ether. The ether solution of the base was added to a solution of 8 g fumaric acid in 150 ml meth-

EXAMPLE 26

β-[2-(4-methoxyphenyl)-2-hydroxyethylamino]-3-(β,β-dimethylacrylylamino)propiophenone

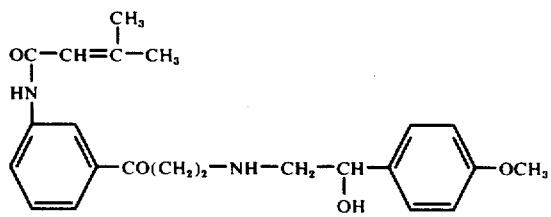

24 g β-dimethylamino-3-(3,3-dimethyl-acryloylamino)-propiophenone hydrochloride and 11 g of 2-(4-methoxyphenyl-2-hydroxy-ethylamine were stirred at 50° C for a period of 30 minutes into a 300 ml water-methanol mixture (2:1). The oil that separated out was decanted and dissolved in ether. The ether solution of the base was added to a solution of 8 g of fumaric acid in 150 ml methanol. The fumarate after a short time crystallized out. m.p. 141°–143° C.

EXAMPLE 27

β-[2-(4-Fluorophenyl)-2-hydroxyethylamino]-3-(β,β-dimethylacrylylamino)propiophenone

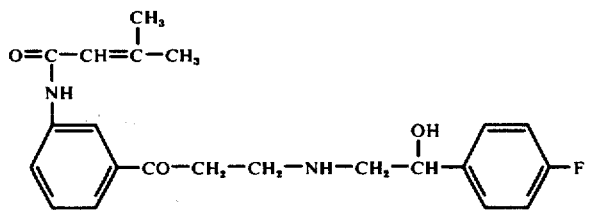

31 g β-dimethylamino-3-(3,3-dimethyl-acryloylamino)-propiophenone hydrochloride and 16.5 g of 2-(4-fluorophenyl)-2hydroxy-ethylamine were stirred for a period of 30 minutes at 50° C in 300 ml of a water-methanol mixture (2:1). The oil that separated out was decanted and the base was dissolved in ether. The ether solution was added to a solution of 8 g fumaric acid in 150 ml methanol. After a short period of time, the fumarate crystallized out. m.p. 148° C.

anol. The fumarate after a short time crystallized out and was recrystallized from methanol. m.p. 164°–167° C.

EXAMPLE 28

β-[1-(4-hydroxy-phenyl-ethylamino]-3-(3,3-dimethyl-acryloylamino)-propiophenone

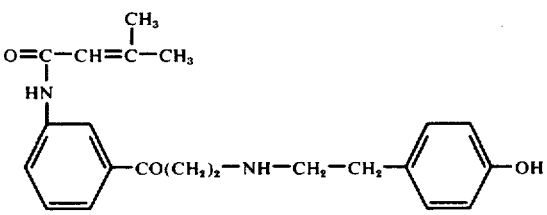

35 g β-dimethylamino-3-(3,3-dimethyl-acryloylamino)-propiophenone.HCl and 15 g 2-(4-hydroxy-phenyl)-ethylamine were stirred at 50° C for 30 minutes in 300 ml of a water-methanol mixture (2:1). The mass was then decanted from the solvent and the remaining solidified substance was dissolved in methanol. The fumarate was precipitated from the solution with fumaric acid and recrystallized from methanol. m.p. 142°–143° C.

EXAMPLE 29 d,l-β-[1-(4-Hydroxy-phenyl)-1-hydroxy-prophyl-(2)-amino]-3-β,β-dimethyl-acryloylamino-propiophenone

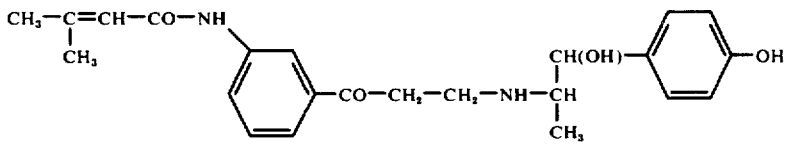

37.3 g d,l-β-[1-(4-hydroxy-phenyl)-1-hydroxy-propyl-(2)-amino]-3-nitro-propiophenone.HCl were hydrogenated in 250 ml methanol in the presence of 5 g palladium/barium sulfate at room temperature and atmospheric pressure. The reduction was discontinued after the calculated amount of hydrogen had been absorbed. The mass was removed from the catalyst by filtration and the solvent was distilled off. The remaining d,l-β-[1-(4-hydroxy-phenyl)-1-hydroxy-propyl-(2)-amino]-3-amino-propiophenone.HCl (m.p. 173°–174° C) was recrystallized from methanol.

20 g of d,l-β-[1-(4-hydroxy-phenyl)-1hydroxy) 2)-amino]-3-amino-propiophenone.HCl were then dissolved in 70 ml dimethylformamide and 70 ml acetone and after adding 4.6 ml pyridine were reacted at room temperature with 6.7 g β,β-dimethylacrylic acid chloride. The d,l-β-[1-(4-hydroxy-phenyl)-1-hydroxy-propyl-(2)-amino]-3-β,β-dimethyl-acryloylamino-propiophenone separated as an oil after 15 minutes upon addition of 200 ml gasoline and was caused to crystallize by treatment with 250 ml water. It then was recrystallized from methanol. m.p. 200° C.

The starting product was in this example formed as follows:

90.7 g of 3-nitroacetophenone, 101.5 g d,l-4-hydroxy-norephedrine. HCl and 19.5 g paraformaldehyde were reacted and refluxed for 4 hours in 400 ml isopropanol. The thus-precipitated d,l-β-[1-(4-hydroxy-phenyl)-1-hydroxy-propyl-(2)-amino]-3-nitro-propiophenone.HCl (m.p. 195° C) was recrystallized from methanol.

EXAMPLE 30 d,l-β-[1-(4-hydroxy-phenyl)-hydroxy-propyl-(2)-amino]-3-acetoxy-propiophenone

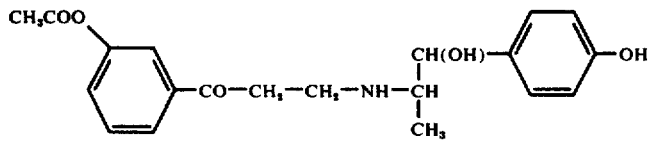

17.8 g (0.1 mol) 3-acetoxy-acetophenone, 4 g paraformaldehyde and 20.3 g (0.1 mol) d,l-4-hydroxy-norephedrine.HCl were subjected to boiling and refluxing for 4 hours in 150 ml isopropanol. After 2 hours additional 2 g of paraformaldehyde were added. The solvent was then removed by distillation and the residue was shaken with water and ether. The separated oily HCl salt was dissolved in isopropanol, precipitated with ether and recrystallized from ethanol. m.p. 173°–174° C.

EXAMPLE 31 l-β-[1-Phenyl-1-hydroxy-propyl-(2)-amino]-3-β,β-dimethylacryloyloxy-propiophenone

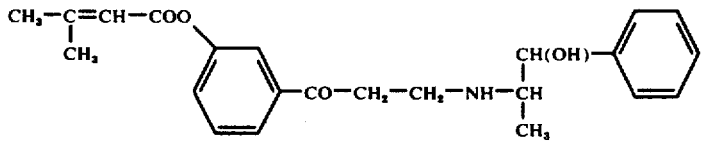

21.8 g (0.1 mol) 3-β,β-dimethylacryloyloxy-acetophenone, 3 g paraformaldehyde and 18.7 g (0.1 mol) l-norephedrine.HCl were subjected to boiling and refluxing in 100 ml isopropanol for 3 hours. After one hour another 1.5 g paraformaldehyde were added. After cooling down, the HCl salt precipitated and was recrystallized from methanol. m.p. 189°–190° C.

EXAMPLE 32 d,l-β-[1-(Hydroxy-phenyl)-1-hydroxy-propyl-(2)-amino]-3-β,β-dimethylacryloyloxy-propiophenone

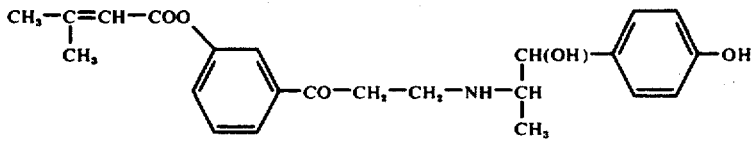

21.8 g (0.1 mol) 3-β,β-dimethylacryloyloxy-acetophenone, 3 g paraformaldehyde and 20.5 g (0.1 mol) d,l-4-hydroxy-norephedrine were subjected to boiling and refluxing for 3 hours in 100 ml isopropanol. After 1 hour an additional 1.5 g of paraformaldehyde were added. The solvent was distilled off and the residue was shaken with water and ether. The initially oily HCl salt solidified and was then recrystallized from isopropanol. m.p. 173°–174° C.

EXAMPLE 33 d,l-β-[1-(4-Hydroxyphenyl)-1-hydroxypropyl-(2)-amino]-3-(β,β-dimethylacryloylamino)-propiophenone

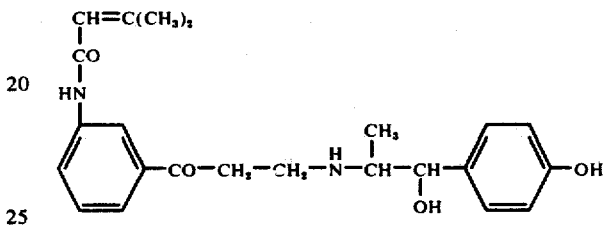

7 g d,l-β-[1-(4-hydroxyphenyl)-1-hydroxypropyl-(2)-amino]-3-(β,β-dimethylacryloylamino)-acrylophenone dissolved in 100 ml acetic acid were hydrogenated with 0.5 g platinum oxide at a temperature between 30° and 40° C until the calculated theoretical amount of hydrogen had been absorbed. The mass was then removed from the catalyst by filtration and the filtrate was acidified with an isopropanol solution of HCl. The HCl salt was precipitated with ether and recrystallized with a small amount of methanol. The yield was 5 g. m.p. 200° C.

The d,l-β-[1-(4-hydroxyphenyl)-1-hydroxypropyl-(2)-amino]-3-(β,β-dimethylacrylamino)-acrylophe-none which was used as the starting product was obtained as follows:

22 g (3-(β,β-dimethylacryloylamino)-acetophenone in 400 ml dioxane were reacted with 10 ml of a 33% finely dispersed sodium in xylene which was added dropwise, at a temperature of 30°–40° C.

EXAMPLE 34

1-β-[1-Phenyl-1-hydroxy-propyl-(2)-amino]-3-cinnamoylamino-propiophenon

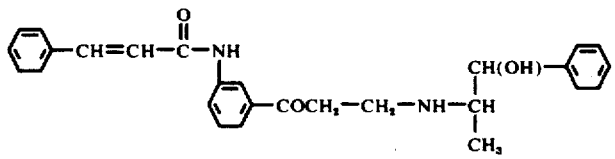

19.3 g 1-β-[1-phenyl-1-hydroxy-propyl-(2)-amino]-3-amino-propiophenone.HCl was dissolved in 120 ml of dimethylformamide and after adding 4.1 ml pyridine is reacted at room temperature with 9.8 g of cinnamic acid chloride dissolved in 25 ml acetone. The 1-β-[1-phenyl-1-hydroxy-propyl-(2)-amino]-3-cinnamoylamino-propiophenone-hydrochloride was caused to crystallize after 15 minutes by adding 300 ml of a hydrochloric acid of about 3% concentration and is then recrystallized from methanol. m.p. 122°–127° C.

EXAMPLE 35

1-β-[1-Phenyl-1-hydroxy-propyl-(2)-amino]-3-(4-methyl-cinnamoylamino-propiophenone

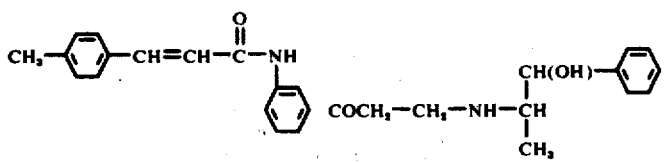

16.7 g 1-β-[1-phenyl-1-hydroxy-propyl-(2)-amino]-3-amino-propiophenone.HCl were dissolved in 120 ml dimethylformamide and after adding 4 ml pyridine were reacted with 9 g of 4-methylcinnamic acid chloride dissolved in 25 ml acetone. The reaction is carried out at room temperature. The 1-β-[1-phenyl-hydroxy-propyl-(2)-amino]-3-(4-methylcinnamoylamino)-propiophenone-hydrochloride was caused to crystallize after 15 minutes by adding 300 ml of hydrochloric acid of about 3% concentration. It was then recrystallized from ethanol and a few drops isopropanol-hydrochloric acid. m.p. 144° C.

EXAMPLE 36 d,l-β-[1-(4-Hydroxyphenyl)-1-hydroxypropyl-(2)-amino]-3-(4-methylcinnamoylamino)-propiophenone

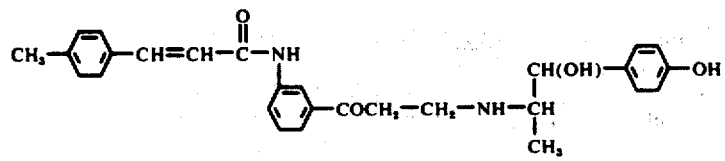

17.5 g d,l-β-[1-(4-hydroxyphenyl)-1-hydroxypropyl-(2)-amino]-3-amino-propiophenone.HCl were dissolved in 120 ml dimethylformamide and after adding 4 ml pyridine were reacted with 9 g of 4-methylcinnamic acid chloride dissolved in 25 ml acetone. The d,l-β-[1-(4-hydroxyphenyl-1-hydroxypropyl-(2)-amino]-3-(4-methylcinnamoylamino)-propiophenone-hydrochloride was caused to crystallize after 15 minutes by adding 300 ml of hydrochloric acid of about 3% concentration. The compound was then recrystallized from isopropanol with a few drops of isopropanol-hydrochloric acid.

EXAMPLE 37 d,l-β-[1-(4-Hydroxyphenyl)-1-hydroxypropyl-(2)-amino]-3-cinnamoylamino-propiophenone

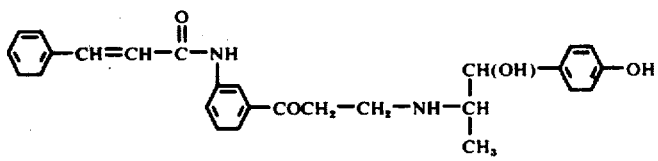

17.5 g d,l-β-[1-(4-hydroxyphenyl)-1-hydroxypropyl-(2)-amino]-3-amino-propiophenone.HCl were dissolved in 120 ml dimethylformamide and after adding 4 ml pyridine reacted with 8.3 g of cinnamic acid chloride dissolved in 25 ml acetone. The d,l-β-[1-(4-hydroxyphenyl)-1hydroxypropyl-(2)-amino]-3-cinnamoylamino-propiophenone-hydrochloride was caused to crystallize after 15 minutes by adding 300 ml of hydrochloric acid of about 3% concentration. It was dissolved in ethanol and precipitated with H₂O followed by drying for 3 hours at 70° C. m.p. 147°–148° C.

EXAMPLE 38 d,l-β-[1-(4-Hydroxyphenyl)-1-hydroxypropyl-(2)-amino]-3-(4-chlorcinnamoylamino)-propiophenone

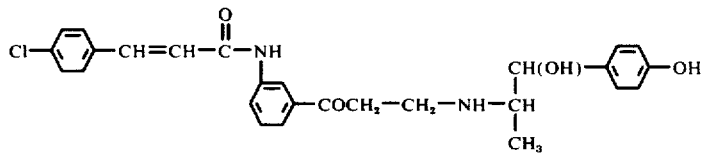

17.5 d,l-β-[1-(4-hydroxyphenyl)-1-hydroxypropyl-(2)-amino]-3-amino-propiophenone.HCl were dissolved in 120 ml dimethylformamide and after adding 4 ml pyridine was reacted with 10.5 g of 4-chlorocinnamic acid chloride dissolved in 25 ml acetone. The reaction was carried out at room temperature. The d,l-β-[1-(4-hydroxyphenyl)-1-hydroxypropyl)-(2)-amino]-3-(4-chlorocinnamoylamino)-propiophenone-hydrochloride was caused to crystallize after 15 minutes by adding 300 ml hydrochloric acid of about 3% concentration. It was recrystallized from isopropanol and a few drops of isopropanol-HCl. m.p. 160°–162° C.

EXAMPLE 39 l-β-[1-Phenyl-1-hydroxy-propyl-(2)-amino]-3-(4-chlorcinnamoylamino)-propiophenone

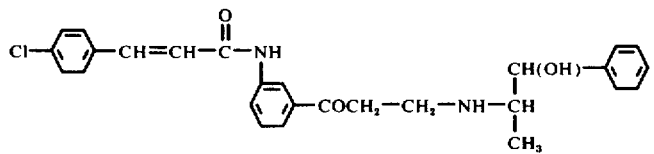

16.7 g l-β-[1-phenyl-1-hydroxy-propyl-(2)-amino]-3-amino-propiophenone.HCl were dissolved in 120 ml dimethyl-formamide and after adding 4 ml pyridine were reacted with 4-chlorocinnamic acid chloride at room temperature dissolved in 25 ml acetone. The l-β-[1-phenyl-1-hydroxy-propyl-(2)-amino]-3-(4-chlorocinnamoylamino)-propiophenone-hydrochloride was caused to crystallize after 15 minutes by adding about 300 ml of hydrochloric acid of about 3% concentration and was then recrystallized from isopropanol with a small amount of isopropanol-hydrochloric acid. m.p. 106° C. (decomposition).

EXAMPLE 40 l-β-[1-Phenyl-1-hydroxy-propyl-(2)-amino]-3-(2-chlorcinnamoylamino)-propiophenone

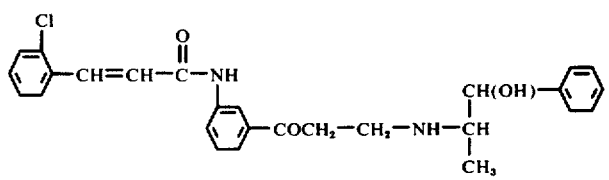

16.7 g l-β-[1-phenyl-1-hydroxy-propyl-(2)-amino]-3-amino-propiophenone.HCl were dissolved in 120 ml dimethylformamide and after adding 4 ml pyridine were reacted at room temperature with 2-chlorocinnamic acid chloride dissolved in 25 ml acetone. The l-β-[1-phenyl-1-hydroxy-(2)-amino]-3-(2-chlorocinnamoylamino)-propiophenone-hydrochloride was caused to crystallize after 15 minutes by adding 300 ml of hydrochloric acid of about 3% concentration and was recrystallized from isopropanol with a small amount of isopropanol-hydrochloric acid. m.p. 142°–146° C (decomposition).

EXAMPLE 41 d,l-β-[1-(4-Hydroxyphenyl)-1-hydroxypropyl-(2)-amino]-3-(2-chlorcinnamoylamino)-propiophenone 17.5 g d,l-β-[1-(4-hydroxyphenyl)-1-hydroxypropyl-(2)amino]-3-amino-propiophenone.HCl were dissolved in 120 ml dimethylformamide and after adding 4 ml pyridine were reacted at room temperature with 2-chlorocinnamic acid chloride dissolved in 25 ml acetone. The d,l-β-[1-(4-hydroxyphenyl)-1-hydroxypropyl-(2)-amino]-3-(2-chlorocinnamoylamino)-propiophenone-hydrochloride was caused to crystallize after 15 minutes by adding 300 ml of hydrochloric acid of about 3% concentration and is recrystallized from isopropanol with a small amount of isopropanolic hydrochloride. m.p. 168°–170° C.

EXAMPLE 42

1-β-[1-Phenyl-1-hydroxy-propyl-(2)-amino]-3-(3-methoxycinnamoylamino)-propiophenone

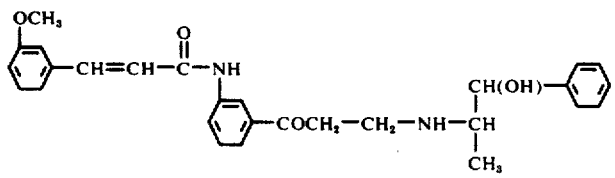

16.7 g 1-β-[1-phenyl-1-hydroxy-propyl-(2)-amino]-3-amino-propiophenone.HCl were dissolved in 120 ml dimethylformamide and after adding 4 ml pyridine were reacted with 9.8 g 3-methoxycinnamic acid chloride dissolved in 25 ml acetone. The reaction is carried out at room temperature. The 1-β-[1-phenyl-1-hydroxy-propyl-(2)-amino]-3-(3-methoxycinnamoylamino)-propiophenone-hydrochloride was caused to crystallize after 15 minutes by adding 300 ml of hydrochloric acid of about 3% concentration and was recrystallized from isopropanol with isopropanolic hydrochloric acid. The solution was covered with ether. m.p. 172°–175° C.

EXAMPLE 43 d,l-β-[1-(4-Hydroxyphenyl)-1-hydroxypropyl-(2)-amino]-3-(3-methoxycinnamoylamino)-propiophenone

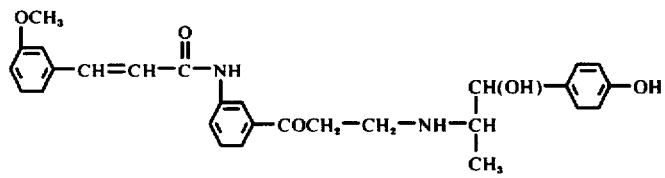

17.5 g d,l-β-[1-(4-hydroxyphenyl)-1-hydroxypropyl-(2)-amino]-3-amino-propiophenone.HCl were dissolved in 120 ml dimethylformamide and after adding 4 ml pyridine were reacted at room temperature with 3-methoxycinnamic acid chloride dissolved in 25 ml acetone. The d,l-β-[1-(4-hydroxyphenyl)-1-hydroxypropyl-(2)-amino]-3-(3-methoxycinnamoylamino)-propiophenone-hydrochloride was caused to crystallize after 15 minutes by adding a 3% hydrochloic acid. It was recrystallized from isopropanol and isopropanolic hydrochloric acid. The solution is covered with ether. m.p. 193°–195° C.

EXAMPLE 44 d,l-β-[1-(4-Hydroxyphenyl)-1-hydroxypropyl-(2)-amino]-3-(α-methylcinnamoylamino-propiophenone

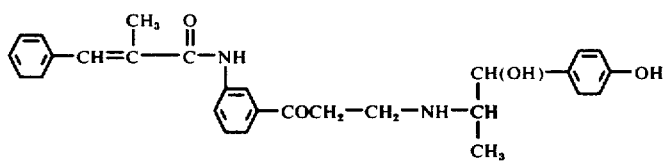

17.5 g d,l-β-[1-(4-hydroxyphenyl)-1-hydroxypropyl-(2)-amino]-3-amino-propiophenone.HCl were dissolved in 120 ml dimethylformamide, and after adding 4 ml pyridine were reacted at room temperature with 9 g of α-methylcinnamic acid chloride dissolved in 25 ml acetone. The d,l-β-[-(4-hydroxyphenyl)-1-hydroxypropyl-(2)-amino]-3-(α-methylcinnymoylamino)-propiophenone-hydrochloride was caused to crystallize after 15 minutes by adding 300 ml of hydrochloric acid of about 3% concentration and was recrystallized from isopropanol with isopropanolic hydrochloric acid. m.p. 178°–180° C.

EXAMPLE 45

1-β-[1-Phenyl-1-hydroxy-propyl-(2)-amino]-3-(4-methoxycinnamoylamino)-propiophenone

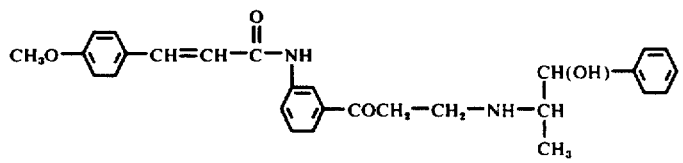

16.7 g 1-β-[1-phenyl-1-hydroxy-propyl-(2)-amino]-3-amino-propiophenone.HCl were dissolved in 120 ml dimethylformamide and after adding 4 ml pyridine were reacted at room temperature with 9.8 g 4-methoxycinnamic acid chloride dissolved in 25 ml acetone. The 1-β-[1-phenyl-1-hydroxy-propyl-(2)-amino]-3-(4-methoxycinnamoylamino)-propiophenone-hydrochloride was caused to crystallize after 15 minutes by adding 300 ml of hydrochloric acid of about 3% concentration and was recrystallized from isopropanol in a

EXAMPLE 46 d,l-β-[1-(4-Hydroxyphenyl)-1-1-hydroxypropyl-(2)-amino]-3-(4-methoxycinnamoylamino)-propiophenone

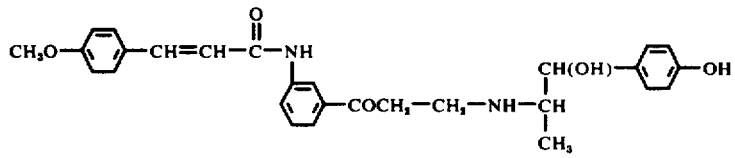

17.5 g d,l-μ-[1-(4-hydroxyphenyl)-1-hydroxypropyl-(2)-amino]-3-amino-propiophenone.HCl were dissolved in 120 ml dimethylformamide and after adding 4 ml pyridine were reacted at room temperature with 9.8 g 4-methoxycinnamic acid chloride dissolved in 25 ml acetone. The d,l-β-[1-(4-hydroxyphenyl)-1-hydrochloride was caused to crystallize after 15 minutes by adding 300 ml hydrochloric acid of about 3% concentration and was recrystallized from isopropanol in a small amount of isopropanolic hydrochloric acid. The solution was protected by ether and was left standing for several days. m.p. 183°-184° C.

EXAMPLE 47

β-[1-Phenyl-1-hydroxy-ethyl-(2)-amino]-3-(β,β-dimethylacryloylamino)-propiophenone

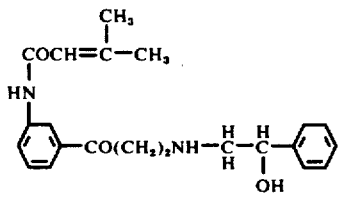

24 g (0.11 mol) 3-(β,β-dimethylacryloylamino)-acetophenone, 17.4 g (0.1 mol) 1-phenyl-1-hydroxyethyl-(2)-amino-hydrochloride and 3.6 g paraformaldehyde were heated and refluxed for 7 hours in 70 ml isopropanol. It was reacted with ammonia while cooling by ice, and then diluted with water. The base was taken up with ether. After drying of the ether phase, the latter was reacted with gasoline. The base then crystallized in pure form. The fumarate was precipitated from ethanol. m.p. 174° C.

EXAMPLE 48

β-[1-α-Chlorphenyl-1-hydroxy-propyl-(2)-amino]-3-(β,β-dimethylacryloylamino)-propiophenone

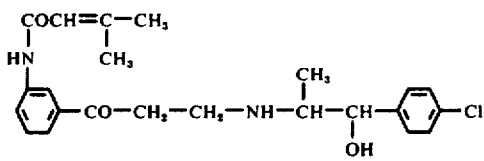

22 g (0.1 mol) 3-(β,β-dimethylacryloylamino)-acetophenone, 21 g (0.1 mol) p-chloronorephedrine-hydrochloride and 3.9 g (0.13 mol) paraformaldehyde were heated and refluxed for 6 hours in 70 ml isopropanol. The base was liberated by reaction with NH₄OH while cooling by ice. It was recrystallized from ether. Subsequently the HCl salt was precipitated from ethanol/ether. m.p. 156°-158° C.

EXAMPLE 49

β-[1-(p-Fluorphenyl)-1-hydroxy-propyl-(2)-amino]-3-(β,β-dimethylacryloylamino)-propiophenone

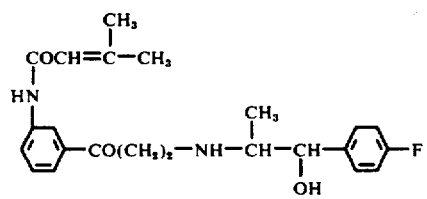

18 g (0.09 mol) 1-(p-fluorophenyl)-1-hydroxy-propyl-2-amino-hydrochloride, 22 g (0.1 mol) 3-(β,β-dimethylacryloylamino)-acetophenone and 3.6 g paraformaldehyde were heated and refluxed for 6 hours in 70 ml isopropanol. The solvent was then distilled off. The residue was taken up in 300 ml acetone whereupon the desired compound crystallizes out. The HCl was purified from the base. The hydrochloride was recrystallized from ethanol/ether. m.p. 166° C.

EXAMPLE 50

β-[1-(p-Methylphenyl)-1-hydroxy-propyl-(2)-amino]-3-(β,β-dimethylacryloylamino)-propiophenone

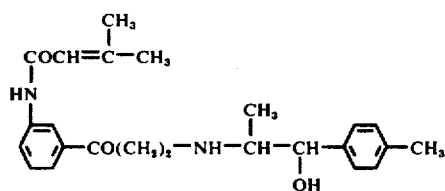

20.5 g (0.1 mol) p-methylnorephedrine-hydrochloride, 22 g (0.1 mol) 3-(β,β-dimethylacryloylamino)-acetophenone, 3.9 g (0.13 mol) paraformaldehyde and 70 ml isopropanol were heated together and refluxed for 6 hours in 70 ml isopropanol. The solvent was subsequently distilled off and the residue taken up in 300 ml acetone. The compound crystallized in impure form. The base was then liberated with aqueous ammonia while cooling with ice and crystallized from ether. The hydrochloride was precipitated from acetone with isopropanolic hydrochloric acid. It crystallized out in pure form. m.p. 136° C.

EXAMPLE 51

β-[1-(p-Methylphenyl)-1-hydroxy-butyl-2-amino]-3-(β,β-dimethylacryloylamino)-propiophenone

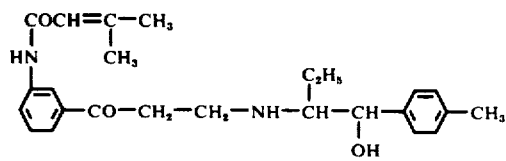

24 g (0.11 mol) 3-(β,β-dimethylacryloylamino)-acetophenone, 21.5 g (0.1 mol) 1-(p-methylphenyl)-1-hydroxy-butyl-(2)-amino-hydrochloride and 3.6 g (0.2 mol) + 1.5 g (0.05 mol) paraformaldehyde were heated and refluxed for 6 hours in 70 ml isopropanol at a pH of 5. The solvent was then distilled off and the residue taken up in acetone. The compound crystalized out of the solution. It was recrystallized twice from methanol-/aceteone m.p. 184°–186° C.

EXAMPLE 52

1-β-[1-Phenyl-1-hydroxy-propyl-(2)-amino]-3-phenoxycarbonylamino-propiophenone

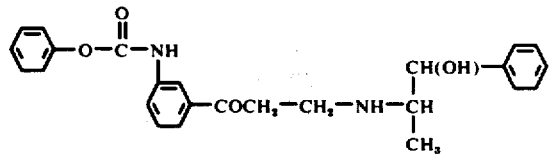

16.7 g 1-β-[1-phenyl-1-hydroxy-propyl-(2)-amino]-3-amino-propiophenone.HCl were dissolved in 120 ml dimethylformamide and after adding 4 ml pyridine were reacted at room temperature with 7.8 g chloroformic acid phenyl ester dissolved in 25 ml acetone. The 1-β-[1-phenyl-1-hydroxy-propyl-(2)-amino]-3-phenoxycarbonylamino-propiophenone-hydrochloride was caused to crystallize after 15 minutes by adding 300 ml of hydrochloric acid of about 3% concentration and was recrystallized from ethanol. m.p. 178°–180° C.

EXAMPLE 53 d,l-β-[1-(4-Hydroxyphenyl)-1-hydroxy-propyl-(2)-amino]-3:phenoxycarbonylamino-propiophenone

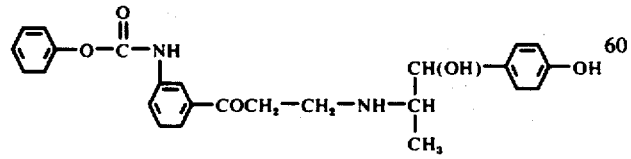

17.5 g d,l-β-[1-(4-hydroxyphenyl)-1-hydroxy-propyl-(2)-amino]-3-aminopropiophenone.HCl were dissolved in 120 ml dimethylformamide and after adding 4 ml pyridine was reacted with 7.8 g of chloroformic acid phenyl ester dissolved in 25 ml acetone. The d,l-β-[1-(4-hydroxyphenyl)-1-hydroxy-propyl-(2)-amino]-3:phenoxy-carbonylamino-propiophenone-hydrochloride was caused to crystallize after 15 minutes by adding 300 ml of hydrochloric acid of about 3% concentration and were recrystallized from ethanol. m.p. 196°–197° C.

EXAMPLE 54

1-β-[1-Phenyl-1:hydroxy-propyl-(2)-amino]-3-(d-Methylcinnamoylamino)-propiophenon

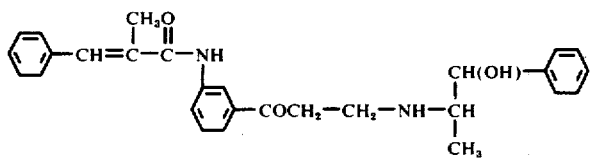

16.7 g 1-β-[1-phenyl-1-hydroxy-propyl-(2)-amino]-3-amino-propiophenone.HCl were dissolved in 120 ml dimethylformamide and after adding 4 ml pyridine were reacted at room temperature with 9 g of α-methylcinnamic acid chloride, dissolved in 25 ml acetone. The 1-β-[1-phenyl-1-hydroxy-propyl-(2)-amino]-3-(α-methylcinnamoylamino)-propiophenone-hydrochloride was caused to crystallize after 15 minutes by adding 300 ml of hydrochloric acid of a 3% concentration and was recrystallized from isopropanol and isopropanolic hydrochloric acid. m.p. 168°–169° C.

Without further analysis, the foregoing will so fully reveal the gist of the present invention that others can by applying current knowledge readily adapt it for various application without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims.

We claim:
1. A compound selected from the group consisting of compounds having the formula

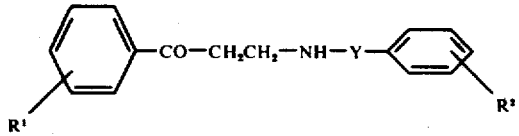

in which $R^1$ is an acetamino, ethoxycarbonylamino, phenoxycarbonylamino, β,β-dimethylacrylylamino, cinnamylamino, 4-methylcinnamylamino, chlorocinnamylamino, methoxycinnamylamino, or α-methylcinnamylamino radical, $R^2$ is a hydrogen, methyl, hydroxyl, methoxy, fluoro, or chloro radical, and Y is a 1-methyl-2-hydroxyethylene or 1-ethyl-2-hydroxyethylene radical, and pharmaceutically acceptable salt of these compounds and optically active isomers and diastereoisomers thereof.

2. A compound as defined in claim 1 which is dl-β-[1-(4-hydroxyphenyl)-1-hydroxypropyl-(2)-amino]-3-(β,β-dimethylacrylylamino)propiophenone.

3. A compound as defined in claim 1 which is β-[1-(4-Methylphenyl)-1-hydroxypropyl-(2)-amino]-3-(β,β-di-methylacrylylamino)propiophenone.

4. A compound as defined in claim 1 which is 1-β-[1-phenyl-1-hydroxypropyl-(2)-amino]-3-(3-methoxycinnamoylamino)propiophenone.

5. A compound as defined in claim 1 which is dl-β-[1-(4-hydroxyphenyl)-1-hydroxypropyl-(2)-amino]-3-(4-chlorocinnamoylamino)propiophenone.

6. A compound as defined in claim 1 which is dl-β-[1-(4-hydroxyphenyl)-1-hydroxypropyl-(2)-amino]-3-(phenoxycarbonylamino)propiophenone.

7. A compound as defined in claim 1 which is 1-β-[1-phenyl-1-hydroxypropyl-(2)-amino]-3-(acetamino)-propiophenone.

* * * * *